United States Patent [19]

Yamamoto et al.

[11] Patent Number: 5,750,979
[45] Date of Patent: May 12, 1998

[54] SIDE FACE EXAMINATION APPARATUS FOR PRESSED ARTICLES, CONVEYOR FOR PRESSED ARTICLES AND EXTERNAL APPEARANCE EXAMINATION APPARATUS FOR PRESSED ARTICLES

[75] Inventors: Taizo Yamamoto, Osaka; Motohiro Yagyu, Nara; Yosihisa Kawaguchi, Kashihara; Akira Nagao, Tenri, all of Japan

[73] Assignee: Japan Elanco Company Limited, Osaka, Japan

[21] Appl. No.: 517,212

[22] Filed: Aug. 21, 1995

[30] Foreign Application Priority Data

Nov. 29, 1994 [JP] Japan ................... 6-294176

[51] Int. Cl.⁶ .......................... B07C 5/342; G01N 21/84
[52] U.S. Cl. ........................... 250/223 R; 209/577
[58] Field of Search ..................... 209/540, 545, 209/576, 577, 701, 905, 919; 474/156; 250/223 R

[56] References Cited

U.S. PATENT DOCUMENTS

| | | |
|---|---|---|
| 3,811,552 | 5/1974 | Wagers, Jr. et al. . |
| 4,354,602 | 10/1982 | Miyoshi et al. ............. 250/223 R |
| 4,472,960 | 9/1984 | Motoyama et al. . |
| 4,582,201 | 4/1986 | Taniguchi et al. ............. 209/701 |
| 5,463,465 | 10/1995 | Yamamoto et al. ............. 209/577 |

FOREIGN PATENT DOCUMENTS

| | | |
|---|---|---|
| 0172663 | 2/1986 | European Pat. Off. . |
| 0605317 | 7/1994 | European Pat. Off. . |
| 0 615 931 A2 | 9/1994 | European Pat. Off. . |
| 0634647 | 1/1995 | European Pat. Off. . |
| 60-114708 | 6/1985 | Japan . |
| 62-111822 | 7/1987 | Japan . |
| 1-320454 | 12/1989 | Japan . |
| 2-107383 | 4/1990 | Japan . |
| 3-67157 | 3/1991 | Japan . |
| 2 108 070 | 5/1983 | United Kingdom . |
| WO 82/03852 | 11/1982 | WIPO . |

*Primary Examiner*—Stephone B. Allen
*Attorney, Agent, or Firm*—Morrison & Foerster LLP

[57] ABSTRACT

Pressed articles are arranged substantially vertical in guide grooves, and transferred to pockets of a conveying drum which is intermittently rotated. The pressed articles are rotated at least more than one turn by a pressed article rotating roller while the pockets are stopped at predetermined positions, and the whole side face of the pressed article is observed by an image pickup apparatus. After changing posture of the pressed articles to be substantially horizontal posture by a posture changing apparatus, front and rear surfaces of the pressed articles are observed by image pickup apparatuses while the pressed articles are held and conveyed on respective sides of equilateral polygons of conveying drums which have equilateral polygonal cross-sections.

28 Claims, 13 Drawing Sheets

A ↕

B ↑

A ↕

← C

B ↑

5,750,979

SIDE FACE EXAMINATION APPARATUS FOR PRESSED ARTICLES, CONVEYOR FOR PRESSED ARTICLES AND EXTERNAL APPEARANCE EXAMINATION APPARATUS FOR PRESSED ARTICLES

FIELD OF THE INVENTION

This invention relates to a side face examination apparatus for pressed articles such as tablets having a substantially circular cross-section, a conveyor for pressed articles which is suitable to the side face examination apparatus, and an external appearance examination apparatus for pressed articles using the side face examination apparatus and the conveyor.

DESCRIPTION OF THE PRIOR ART

Generally, a pressed article such as tablet having a substantially circular cross-section is known as shown in FIGS. 12(a) and 12(b) or FIGS. 13(a) and 13(b). FIG. 12(a) is a plan view of a first tablet when the circular cross-section is horizontal. FIG. 12(b) is a side view of the first tablet shown in FIG. 12(a). Similarly, FIG. 13(a) is a plan view of a second tablet when the circular cross-section is horizontal. FIG. 13(b) is a side view of the second tablet shown in FIG. 13(a).

In case of the first tablet shown in FIGS. 12(a) and 12(b), a cross-section perpendicular to the circular cross-section has substantially elliptical shape. Thus, when an external appearance of the first tablet is examined from two directions shown by arrows A and B in FIG. 12(b), all the inferior matters of the appearance such as adherence of an alien substance, deformation of the shape, inferior printing and so on, can be examined.

On the other hand, in case of the second tablet shown in FIGS. 13(a) and 13(b), a cross-section perpendicular to the circular cross-section has substantially rectangular shape, so that the side face of second tablet is cylindrical. Thus, the whole external appearance of the second tablet can not be examined from two directions shown by arrows A and B in FIG. 13(b). It is necessary to examine the external appearance of the second tablet further from a direction shown by arrow C.

A conventional external appearance examination apparatus for pressed articles, for example, shown in Publication Gazette of Unexamined Japanese Patent Application Hei 2-107383, which can examine the external appearance of the pressed article from the above-mentioned three directions shown by arrows A, B and C, is described referring to FIG. 14.

As shown in FIG. 14, the pressed articles supplied from a hopper 501 are arranged by an arranging apparatus 502 in a manner so that the direction of the circular cross-section of the pressed articles becomes horizontal. The arranged pressed articles are conveyed in a horizontal direction by a conveyor 503. The pressed articles are held on a suction conveyor 504 by suction force of negative pressure.

When rear surfaces of the pressed articles are exposed, picture images of the rear faces of the pressed articles are taken by an image pickup apparatus 505. Furthermore, the pressed articles are transferred from the suction conveyor 504 to another conveyor 506, and the posture of the pressed articles are turned to expose front faces of them. Picture images of the front surfaces of the pressed articles are taken by another image pickup device 507.

When the examinations of the front and rear faces of the pressed articles are completed, the posture of the pressed articles are changed by a posture changing apparatus 508 in a manner so that the circular cross-section becomes vertical. While the pressed articles are rotated by the rotation apparatus 509 under a condition that the circular cross-section is vertical, picture images of side faces of the pressed articles are taken by an image pickup apparatus 510. If the appearance is found to be inferior on at least one of the front, rear and side faces, the pressed article is judged as an inferior article. The inferior article is removed by an inferior article removing apparatus 511. Excellent articles, which are not found to be inferior in appearance, are conveyed to next stage from a shoot 512.

In the above-mentioned conventional external appearance examination apparatus for the pressed articles, the pressed articles contained in the hopper 501 are arranged in a condition that the circular cross-section becomes horizontal for examining the rear and front surfaces of the pressed articles. After that, the posture of the pressed articles are converted to another condition that the circular cross-section is vertical by the posture changing apparatus 508 for examining the side faces of the pressed articles. Furthermore, the hopper 501, the arranging apparatus 502, the conveyor 504, 506, the posture changing apparatus 508, the rotation apparatus 509, the shoot 512 are arranged in the horizontal direction. Thus, the above-mentioned conventional apparatus has a problem that a width of the apparatus becomes wider in a horizontal direction.

The external appearance examination apparatus is generally disposed in a clean room. If the space of the clean room is not so wide, the apparatus occupying a wide space in a horizontal direction wastes valuable space of the clean room. Thus, the width of the apparatus, which is to be disposed in the clean room, should be narrower.

On the other hand, guide rails having substantially the same width as the diameter of the pressed articles are generally used as a conventional conveyor for conveying the pressed articles in an arranged condition. Alternatively, slats with pockets having substantially the same size of the articles are used for conveying the pressed articles.

However, it is generally difficult to convey several kinds of the pressed articles having different widths, diameters or sizes by the same conventional conveyor. Even though the guide rails or slats are interchangeable to convey several kinds of the articles having different sizes or shapes, time for changing the guide rails or slats is wasted and the working ratio of the apparatus is decreased.

The conveyors 504, 506 and the image pickup apparatuses 505, 507, which are used for observing the front and rear surfaces of the pressed articles, have generally well-known configurations. Therefore, there is an opportunity that the side face examination apparatus of the pressed articles, which is configured by the posture changing apparatus 508, the rotation apparatus 509 and the image pickup device 510 and so on, is used in combination with another apparatus different from the above-mentioned conveyors 504, 506 and the image pickup apparatuses 505, 507. Alternatively, there is an opportunity that the side face examination apparatus is used independently. However, a precondition of the use of the side face examination apparatus, the pressed articles supplied to the posture changing apparatus 508 must be arranged in the horizontal direction, previously. Namely, the conventional side face examination apparatus can not examine the pressed articles which are supplied at random.

SUMMARY OF THE INVENTION

This invention is to solve the above-mentioned problems of the prior art, and aims to provide a simply configured and compact side face examination apparatus for pressed articles which can examine the side faces of the pressed articles directly received at random from a hopper or the like, to provide a conveyor for pressed articles which can convey the articles with no relation to the size of the articles to be conveyed, and to provide an external appearance examination apparatus for pressed articles using them.

For achieving the above-mentioned aims, a side face examination apparatus for pressed articles of this invention comprises: an arranging apparatus for arranging pressed articles, which are supplied at random, in a manner so that a cross-section of a pressed article having a largest area is substantially vertical, and having a plurality of guide grooves having a width wider by a predetermined tolerance than a width of the pressed article in a direction perpendicular to the cross-section; a conveying drum intermittently rotated around a horizontal axis, and having pockets arranged for facing the guide grooves and holding the pressed articles, which are arranged by the arranging apparatus, in a manner so that the cross-section is substantially vertical; a pressed article rotating roller disposed at a predetermined position in the inside of the conveying drum, and rotating the pressed articles in the pockets stopped at the predetermined position more than one turn around horizontal axes; and an image pickup apparatus disposed for facing an outer surface of the conveying drum at the predetermined position, and picking up picture images of side faces of the pressed articles in the pockets.

By the side face examination apparatus for pressed articles of this invention configured above, since the width of the guide grooves of the arranging apparatus is wider a predetermined tolerance than the width of the pressed articles in the direction perpendicular to the direction where the pressed articles have the largest cross-sectional area, the pressed articles, which are supplied at random, are arranged in the guide grooves in a manner so that the cross-section having the largest area is substantially vertical. The arranged pressed articles are transferred to the pockets which are arranged for facing the guide grooves, and intermittently conveyed by rotation around the horizontal axis under a condition that the cross-section having the largest area is substantially vertical. The pressed articles in the pockets stopped at the predetermined position are rotated more than one turn around the horizontal axis by the pressed article rotating roller, so that the whole side faces of the pressed articles are observed the the image pickup apparatus. As a result, it is not necessary to arrange the pressed articles previously in a manner so that the cross-section of the pressed article having the largest area is substantially horizontal. The examination of the side face of the pressed articles becomes easy. Furthermore, since the pressed article rotating roller is disposed in the inside of the conveying drum, and the image pickup apparatus is disposed for facing the conveying drum, the size of the apparatus in a horizontal direction is not much larger than the size of the conveying drum, and the configuration of the side face examination apparatus for pressed articles becomes simple and compact.

In the above-mentioned configuration, it is preferable that the conveying drum comprises a fixed hollow inner sleeve and an outer sleeve rotatably engaged with an outer surface of the inner sleeve with a predetermined tolerance; the pockets are provided on the outer sleeve; connection holes or slits are provided at portions of the inner sleeve facing the guide grooves; and the inside of the inner sleeve is connected to a vacuum suction apparatus. Therefore, the pressed articles arranged in the guide grooves are transferred to the pockets one by one from the lowest point by the negative pressure. The omission of the pocket, in which a pressed article is not contained, hardly ever occurs.

Furthermore, in the above-mentioned configuration, it is preferable that the pressed article rotating roller is rotatably borne on the inner sleeve, and has a plurality of larger diameter portions corresponding to the arrangement of the pockets, the larger diameter portions are protruded from the outer periphery of the inner sleeve. Therefore, the side faces of the pressed articles are largely protruded from the outer surface of the outer sleeve in the examination of the side faces. The side faces of the pressed articles are easily distinguished from the pockets or the outer surface of the outer sleeve in the displayed picture image.

Furthermore, in the above-mentioned configuration, it is preferable that a width of the larger diameter portions of the pressed article rotating roller in a direction parallel to a rotation axis thereof is wider than a width of the pockets in that direction, and centers of the larger diameter portions are inconsistent with centers of the pockets. Therefore, the larger diameter portion covers the bottom of the pocket. Furthermore, there is a difference between lengths of air paths from both sides of the larger diameter portion to the center of the pocket. Thereby, a differential pressure is generated by the difference of the lengths in the air paths. The pressed article is pushed on an edge of the pocket in the air path of shorter length by the differential pressure. Accordingly, by standardizing the edge on which the pressed article is pushed, the quality judgement in the examination of the side face can be made easier.

Alternatively, in the above-mentioned configuration, it is preferable that openings of the pockets are formed substantially as parallelograms, a pair of parallel sides are parallel to the rotation axis of the conveying drum and the other parallel sides are inclined against the rotation axis of the conveying drum. Therefore, the pressed article is pushed on the rear end face against the conveying direction (rotating direction of the conveying drum). As a result, by standardizing the end face on which the pressed article is pushed, the quality judgement in the examination of the side face can be made easier.

Furthermore, in the above-mentioned configuration, it is preferable that each of the guide grooves of the arranging apparatus includes a slanted portion and a straight portion, wherein a width in the slanted portion becomes gradually narrower when the position progresses downward, a width in the straight portion is a width wider by a predetermined tolerance than a width of the pressed articles in a direction perpendicular to the cross-section having the largest area, and a vibration is applied to the arranging apparatus. Therefore, the pressed articles, which are supplied at random, can easily be arranged in the guide grooves.

On the other hand, a conveyor for pressed articles of this invention comprises: a conveying drum having an equilateral polygonal cross-section in a vertical direction, and rotated around a horizontal axis; and connection holes provided at predetermined positions on each side of the equilateral polygon for holding pressed articles by negative pressure via the connection holes in a manner so that a cross-section of the pressed article having a largest area is substantially parallel to the horizontal axis. Therefore, many kinds of pressed articles can be conveyed by the same conveying drum, regardless of the sizes of the pressed articles.

Alternatively, another conveyor for pressed articles of this invention comprises: a conveying drum having an equilateral polygonal cross-section in a vertical direction, and rotated around a horizontal axis; and connection holes and wide use pockets provided at predetermined positions on each side of the equilateral polygon for holding pressed articles by negative pressure via the connection holes in the pockets in a manner so that a cross-section of the pressed article having a largest area of the pressed articles is substantially parallel to the horizontal axis. Therefore, many kinds of pressed articles can be conveyed by the same conveying drum, regardless of the sizes of the pressed articles.

In the above-mentioned configuration, it is preferable that each wide use pocket has a portion parallel to a rotation direction of the conveying drum and a substantially V-letter shaped portion having an apex angle of substantially 90 degrees which has an apex at a point distant a predetermined distance from center of the connection hole in the rotation direction. Therefore, a side face of the pressed article contacts edges of the V-letter shaped portion, and the connection hole positions in the vicinity of the center of the pressed article, regardless of the sizes of the pressed articles. The pressed articles are stably held in the wide use pocket by absorption of the negative pressure via the connection hole.

Furthermore, in the above-mentioned configuration, it is preferable that the wide use pockets are formed on a block having a substantially rectangular cross-section in each direction, and each block is interchangeably fixed on a side of the equilateral polygon of the conveying drum. Therefore, many kinds of pressed articles having different sizes can be conveyed by the same conveyor when several kinds of the blocks respectively having different size of wide use pocket are prepared.

Still another conveyor for pressed articles of this invention comprises: an arranging apparatus for arranging pressed articles, which are supplied at random, in a manner so that a cross-section of the pressed article having a largest area is substantially vertical, and having a plurality of guide grooves which have a width wider by a predetermined tolerance than a width of the pressed articles in a direction perpendicular to the cross-section; a first conveying drum intermittently rotated around a horizontal axis, and having first pockets arranged for facing the guide grooves and holding the pressed articles, which are arranged by the arranging apparatus, in a manner so that the cross-section of the pressed article having a largest area is substantially vertical; a posture changing apparatus disposed below the first conveying drum, having second pockets arranged for facing the first pockets, and changing posture of the pressed articles in a manner so that a direction of the cross-section of the pressed article having the largest area is changed from substantially vertical to substantially horizontal; and a second conveying apparatus disposed below the posture changing apparatus, having an equilateral polygonal cross-section in the vertical direction, and rotated around a horizontal axis, wherein connection holes are provided at predetermined positions facing the second pockets on each side of the equilateral polygon for holding the pressed articles in a manner so that the cross-section of the pressed articles is substantially parallel to the horizontal axis by negative pressure via the connection holes. Therefore, the pressed articles, which are supplied at random, can be arranged and conveyed in a manner so that the cross-section having the largest area is substantially parallel to the rotation axis of the conveying drum. Furthermore, the arranging apparatus, the first conveying drum, the posture changing apparatus and the second conveying drum are arranged in a substantially vertical direction, so that the size of the apparatus in the horizontal direction is not so much larger than the size of the conveying drum. The configuration of the conveyor for pressed articles becomes simple and compact.

Alternatively, the afore-mentioned conveying drum having the wide use pockets can be used as the second conveying drum in the above-mentioned conveyor for pressed articles. Therefore, many kinds of the pressed articles can be conveyed by the same conveying drum, regardless of the sizes of the pressed articles.

Furthermore, in the above-mentioned configuration, it is preferable that the posture changing apparatus comprises a rotating drum rotating around a horizontal axis and having the second pockets, and a guide plate provided for facing an outer surface of the drum with a predetermined tolerance, the guide plate has slanted grooves which contacts pressed articles protruded from the second pockets and slanted from a position on an upper end of the guide plate where the second pockets are not covered to a position where the second pockets are completely covered. Therefore, when the drum rotates around the horizontal axis, the pressed articles, which are protruded from the second pockets, contact the slanted edges of the grooves of the guide plate. When the drum further rotates, the pressed articles gradually fall sideways in the axial direction, and finally the posture of the pressed articles can be changed in a manner so that the cross-section of the largest area is substantially horizontal.

On the other hand, an external appearance examination apparatus for pressed articles of this invention comprises the afore-mentioned arranging apparatus, the conveying drums, the pressed article rotating roller, the image pickup apparatuses, and the posture changing apparatus. Therefore, the external appearance examination apparatus for pressed articles operates the operations of the above-mentioned side face examination apparatus for pressed articles and conveyor for pressed articles. Furthermore, the posture changing apparatus is disposed below the first conveying drum. The posture of the pressed articles can be changed in a manner so that a direction of the cross-section having the largest area is changed to substantially horizontal from substantially vertical. The second conveying drum is disposed below the posture changing apparatus, and the third conveying drum is disposed below the second conveying drum. The front and rear surfaces of the pressed articles which are conveyed by the second and third conveying drums are examined by the second and third image pickup apparatuses. Not only the side face but also the front and rear surfaces of the pressed articles can be examined. Furthermore, the arranging apparatus, the first conveying drum, the posture changing apparatus, the second conveying drum, the third conveying drum and the inferior article removing apparatus are arranged in substantially vertical direction, so that the size of the apparatus in the horizontal direction is not so much larger than the size of the conveying drum. The configuration of the external appearance examination apparatus becomes simple and compact.

Furthermore, in the above-mentioned configuration, it is preferable to comprise an inferior article removing apparatus which is disposed below the third conveying drum, has third pockets provided at positions facing the second connection holes or the second wide use pockets and having an area larger than a largest cross-sectional area of the pressed articles and has third connection holes provided in the third pockets for blasting a compressed air. Therefore, an inferior article in which an inferior is found on at least one of the side face, first and second surface can be removed by blasting the compressed air through the third connection hole.

DETAILED DESCRIPTION OF THE INVENTION

Figure 1:
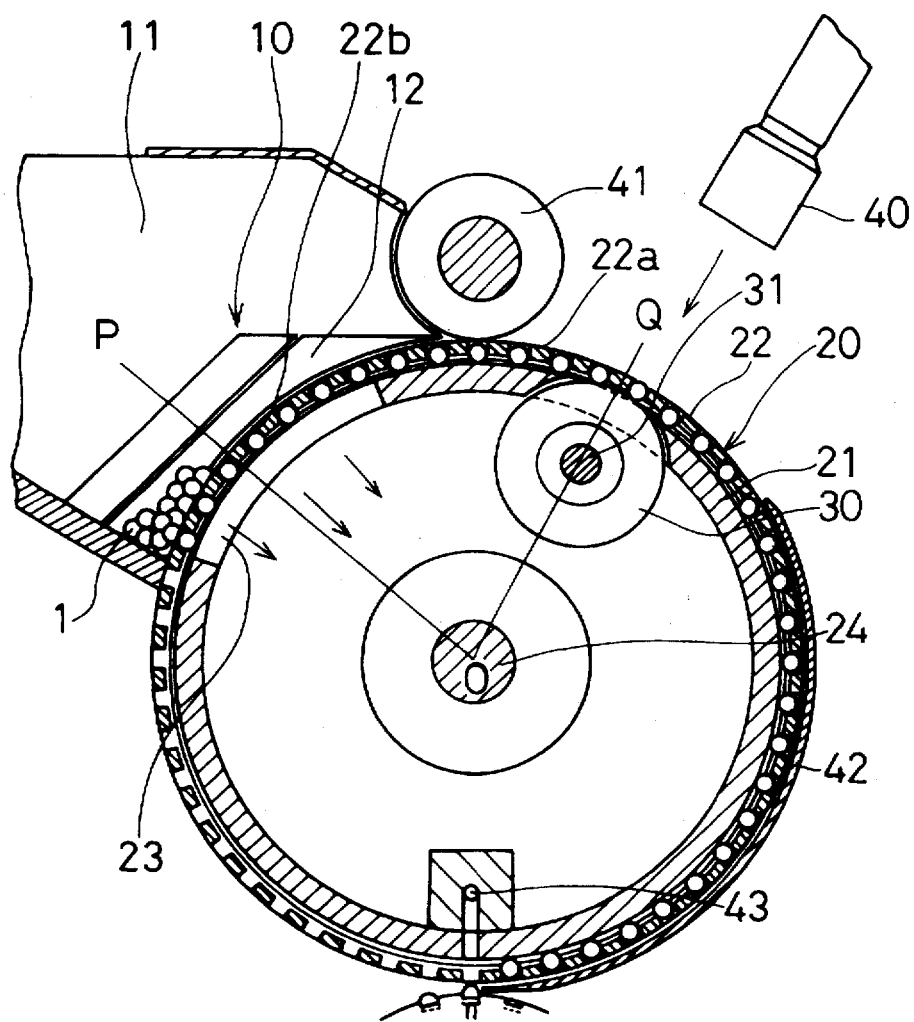
FIG. 1 is a cross-sectional side view showing a configuration of an embodiment of a side face examination apparatus for pressed articles of this invention.
Figure 2:
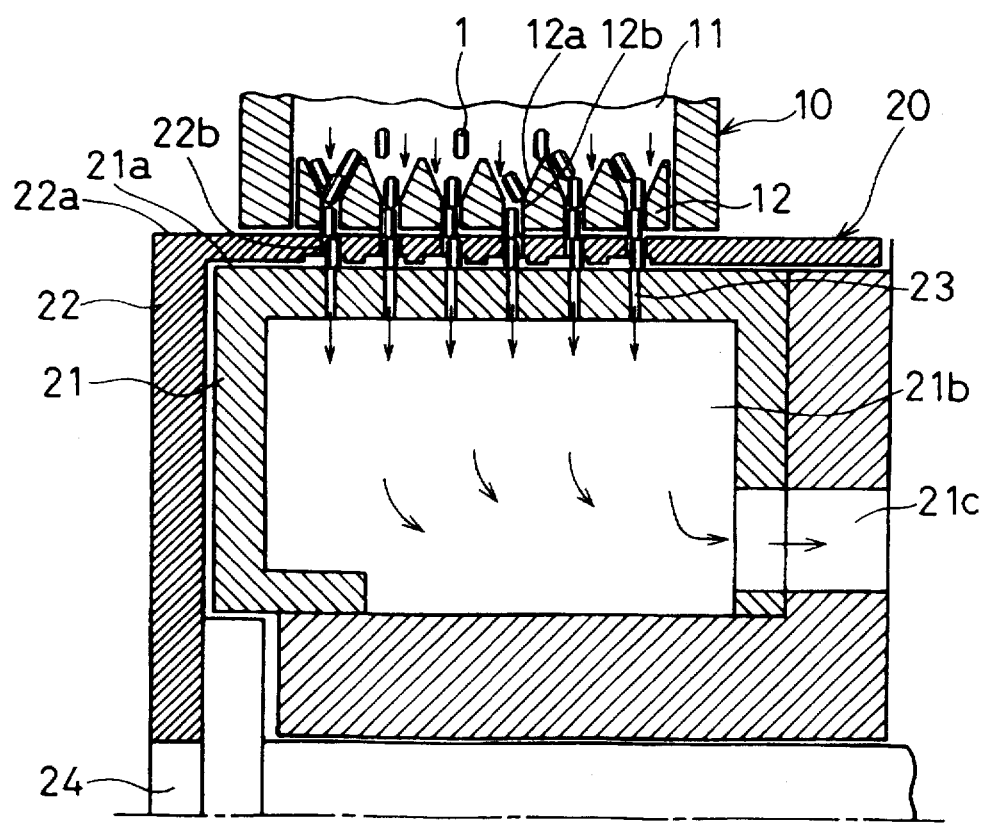
FIG. 2 is a cross-sectional view taken along line O–P in FIG. 1.
Figure 3:
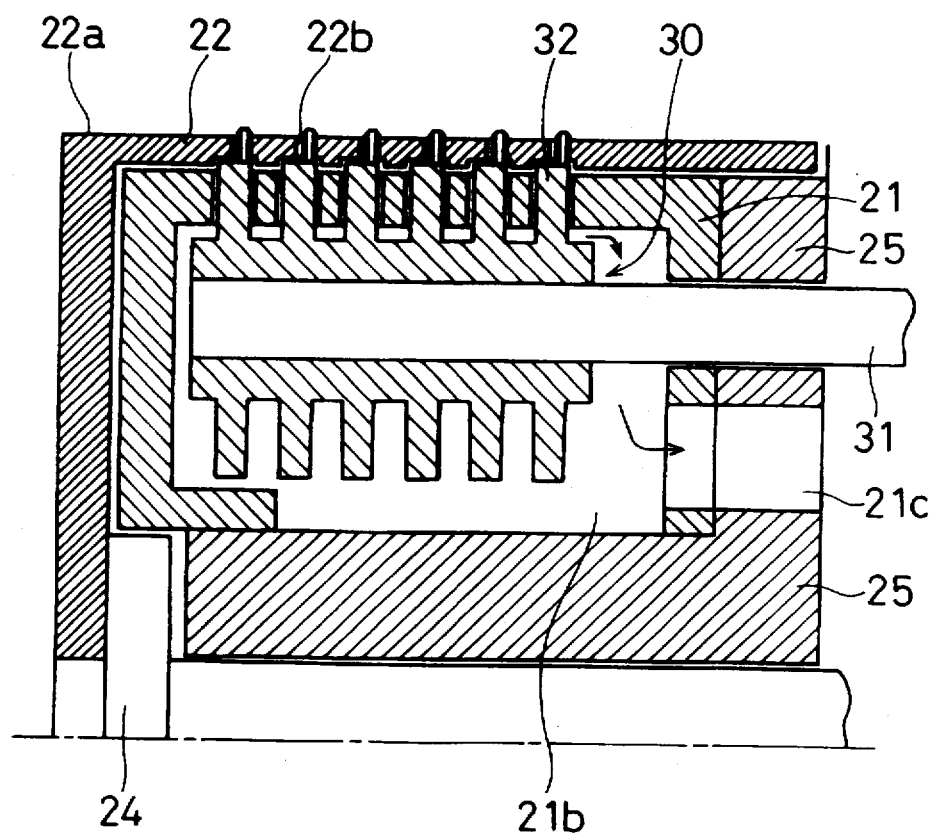
FIG. 3 is a cross-sectional view taken along line O–Q in FIG. 1.

An embodiment of a side face examination apparatus for pressed articles of this invention is described referring to FIGS. 1 to 3. FIG. 1 is a cross-sectional side view showing a configuration of the side face examination apparatus for pressed articles, FIG. 2 is a cross-sectional view taken along line O–P in FIG. 1, and FIG. 3 is a cross-sectional view taken along line O–Q in FIG. 1.

As shown in FIG. 1, the side face examination apparatus for pressed articles of this invention comprises an arranging apparatus 10, a conveying drum 20, a pressed article rotating roller 30, an image pickup apparatus 40, a brush roller 41 and a guide plate 42. The arranging apparatus 10 has a container portion 11 for containing pressed articles 1 which are supplied from a hopper or the like (not shown in the figure) at random. A plurality of guide grooves 12 are formed at the bottom of the container portion 11 and arranged in a horizontal direction.

As shown in FIG. 2, each guide groove 12 has a slanted portion 12a and a straight portion 12b. In the slanted portion 12a, a width at an upper end is the widest and the width becomes gradually narrower when a position progresses downward. In the straight portion 12b, the width is a predetermined constant value which is wider by a predetermined tolerance than a width of the pressed articles 1 in a direction perpendicular to a cross-section having the largest cross-sectional area. By such a configuration, the pressed articles 1 are arranged in the guide grooves 12 in a manner so that the a cross-section of the pressed articles 1 having the largest cross-sectional area becomes substantially vertical. It is preferable that a vibration is applied to the arranging apparatus 10 for easily arranging the pressed articles 1.

As shown in FIGS. 1, 2 and 3, the conveying drum 20 is comprised of a fixed hollow inner sleeve 21, a rotatable outer sleeve 22 and a rotation shaft 24. The inner sleeve 21 has a cylindrical outer surface and is held in a manner so that a center axis becomes horizontal. The outer sleeve 22 has a cylindrical shape and engages with an outer surface 21a of the inner sleeve 21 with a predetermined tolerance. The rotation shaft 24 is borne in a horizontal direction for bearing the rotation of the outer sleeve 22 in a vertical plane. An inside 21b of the inner sleeve 21 is connected to a vacuum suction apparatus (not shown in the figure) via a connection pipe 21c.

As shown in FIG. 2, slits 23 are formed at portions of the inner sleeve 21 which face the guide grooves 12. A plurality of lines of pockets 22b are arranged on an outer surface 22a of the outer sleeve 22 for facing the guide grooves 12 of the arranging apparatus 10. Thus, air flows, which flow from the guide grooves 12 through the pockets 22b, connection holes or slits 23, inside 21b of the inner sleeve 21, and the connection pipe 21c, are generated. The pressed articles 1 arranged in the guide grooves 12 are transferred to the pockets 22b one by one at the bottom by negative pressure. Each pocket 22b holds the pressed article 1 in a manner so that the cross-section having the largest cross-sectional area becomes substantially vertical and a direction perpendicular to the cross-section is substantially parallel to the rotation axis of the rotation shaft 24. As a result, omission of the pressed article 1 in the pocket 22 will not occur.

The brush roller 41 is disposed for contacting the outer surface 22a of the outer sleeve 22 for removing surplus pressed articles 1 getting on the outer surface 22a of the outer sleeve 22. By the operation of the brush roller 41, the pressed articles 1 are not contained more than two in each pocket 22b, or the pressed articles are not contained in an abnormal condition in the pocket 22b. The guide plate 42, which is disposed outside the outer sleeve 22 with a predetermined gap, guides the pressed articles 1 so as not to drop out from the pocket 22b by gravity.

A compressed air blasting apparatus 43 is provided at a bottom portion in an inside of the conveying drum 20 for forcibly transferring the pressed articles 1 which are conveyed by the conveying drum 20 to another apparatus. The conveying drum 20 is intermittently rotated in a predetermined direction by a predetermined angles by a driving mechanism which is not shown in the figure.

As shown in FIGS. 1 and 3, the pressed article rotating roller 30 is disposed at a predetermined position in the inside of the conveying drum 20, and a rotation shaft 31 in a horizontal direction is rotatably borne by the inner sleeve 21 and a fixed block 25. The rotation shaft 31 and the pressed article rotating roller 30 are independent from the conveying drum 20, and they are continuously rotated in a predetermined direction by another driving mechanism not shown in the figure.

As shown in FIG. 3, the pressed article rotating roller 30 has a plurality of larger diameter portions 32 which are disposed corresponding to the lines of the pockets 22b and protruded outside the outer surface 21a of the inner sleeve 21. Accordingly, the side face of the pressed article 1 in the pocket 22b stopping at the above-mentioned predetermined position is protruded outside the outer surface 22a of the outer sleeve 22. Furthermore, the pressed article 1 is rotated in the predetermined direction by the pressed article rotating roller 30.

The image pickup apparatus 40 is disposed at a position facing the larger diameter portions 32 of the pressed article rotating roller 30. The image pickup apparatus 40 takes a picture image of the side faces of the pressed articles 1 rotated by the pressed article rotating roller 30. The pressed article rotating roller 30 rotates the pressed articles 1 more than one turn, while the conveying drum 20 stops in the intermittent movement. Thus, the whole side faces of the pressed articles 1 can be observed. In the examination of the side face, since the side faces of the pressed articles 1 are largely protruded from the outer surface 22a of the outer sleeve 22, the side faces of the pressed articles 1 can easily be distinguished from the pocket 22b or the outer surface 22a of the outer sleeve 22 in a picture image taken by the image pickup apparatus 40.

As shown in FIG. 3, a width of the larger diameter portion 32 of the pressed article rotating roller 30 in a direction of the shaft 31 is wider than a width of the pocket 22b for covering an opening at the bottom of the pocket 22b. Furthermore, the center of the larger diameter portions 32 and the center of the pocket 22b are inconsistent with each other. Thus, lengths of air paths flown from both sides of the larger diameter portion 32 to the center of the pocket 22b becomes different. When the lengths of the air paths is different, a differential pressure is generated between air flows in the air paths. The pressed article 1 is pushed on an edge of the pocket 22b which is positioned in a shorter air path. By standardizing the edge on which the pressed article 1 is pushed, the quality judgement in the examination of the side face becomes easier.

Alternatively, it is preferable that the shape of the opening of the pocket 22b is a parallelogram. A pair of parallel sides are parallel to the rotation shaft 24, and the other parallel sides are inclined against the rotation direction of the conveying drum 20. In the latter case, the pressed article 1 is pushed on the rear edge in the rotating direction of the conveying drum 20. By standardizing the rear edge on which the pressed article 1 is pushed, the quality judgement in the examination of the side face becomes easier.

Figure 4:
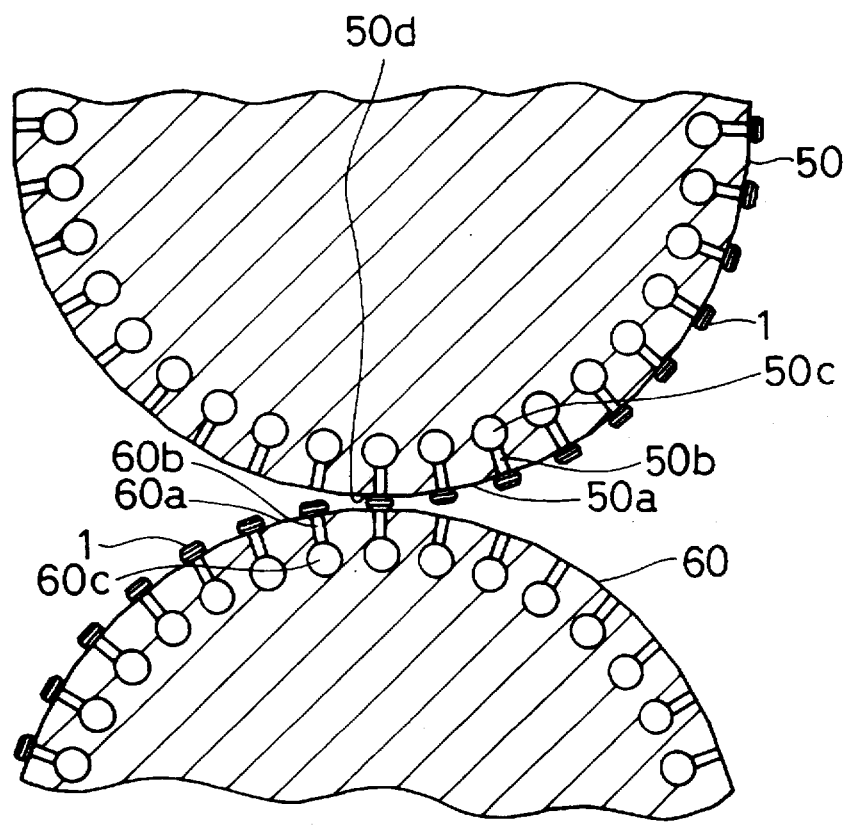
FIG. 4 is a cross-sectional side view showing a configuration of an embodiment of a conveyor for pressed articles of this invention.
Figure 5:
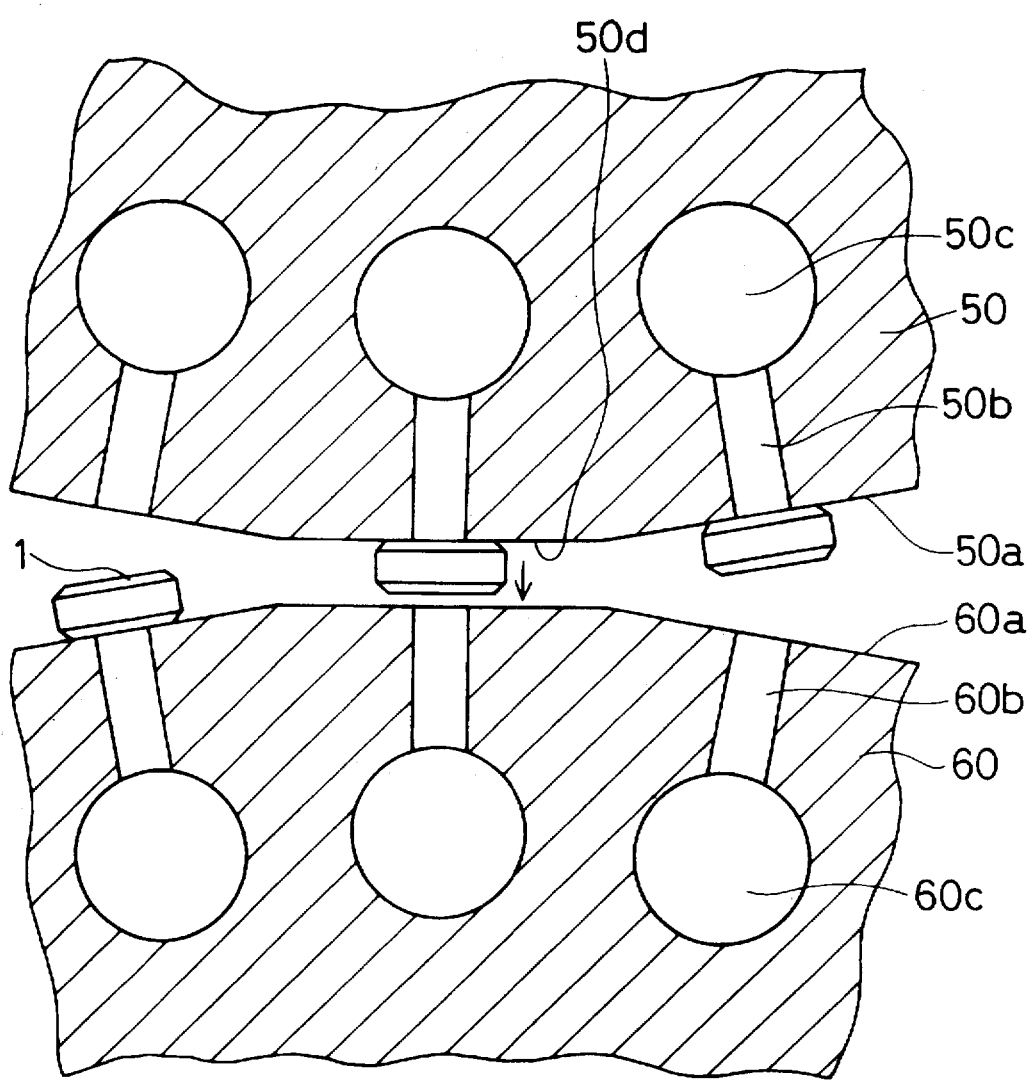
FIG. 5 is an enlarged cross-sectional view of main part in FIG. 4.

Next, an embodiment of a conveyor for pressed articles of this invention is described referring to FIGS. 4 and 5. FIG. 4 is a cross-sectional side view of the conveyor for pressed articles, and FIG. 5 is an enlarged cross-sectional side view of a main part thereof.

As shown in FIGS. 4 and 5, vertical cross-sections of conveying drums 50 and 60 in the conveyor for pressed articles are respectively equilateral polygons. On each side of the equilateral polygons 50a and 60a, connection hole 50b or 60b is provided at a position facing, for example, the pocket 22b of the conveying drum 20 in the above-mentioned side face examination apparatus for pressed articles. The conveying drums 50 and 60 are respectively rotatably borne around horizontal axes. The rotation of the conveying drums 50 and 60 is acceptable to be continuous or intermittent, if the movement of the sides 50a and 60a or the connection holes 50b or 60b are synchronized.

The connection holes 50b and 60b are respectively connected to connection pipes 50c and 60c which are provided parallel to the rotation axes of the conveying drums 50 and 60. The connection pipes 50c and 60c are respectively connected to a vacuum suction apparatus not shown in the figure. Accordingly, the pressed articles 1 are sucked and held on the sides 50a and 60a of the equilateral polygons by negative pressure via the connection holes 50b and 60b and connection pipes 50c and 60c in a manner so that the cross-section of the pressed article 1 having the largest cross-sectional area is substantially parallel to the rotation axes of the conveying drums 50 and 60.

In the conveying drum 50 disposed above the conveying drum 60, when the pressed article 1 held on the side 50a reaches to a lowest portion 50d, the negative pressure in the connection hole 50c at the lowest portion 50d is released. Thus, the pressed article 1 falls by gravity to be transferred to the conveying drum 60. Alternatively, it is preferable not only to release the negative pressure in the connection hole 50c at the lowest position 50d but also to supply positive pressure (to supply compressed air) to the connection hole 50c at the lowest portion 50d so as to transfer the pressed article 1 to the conveying drum 60, certainly.

Figure 6:
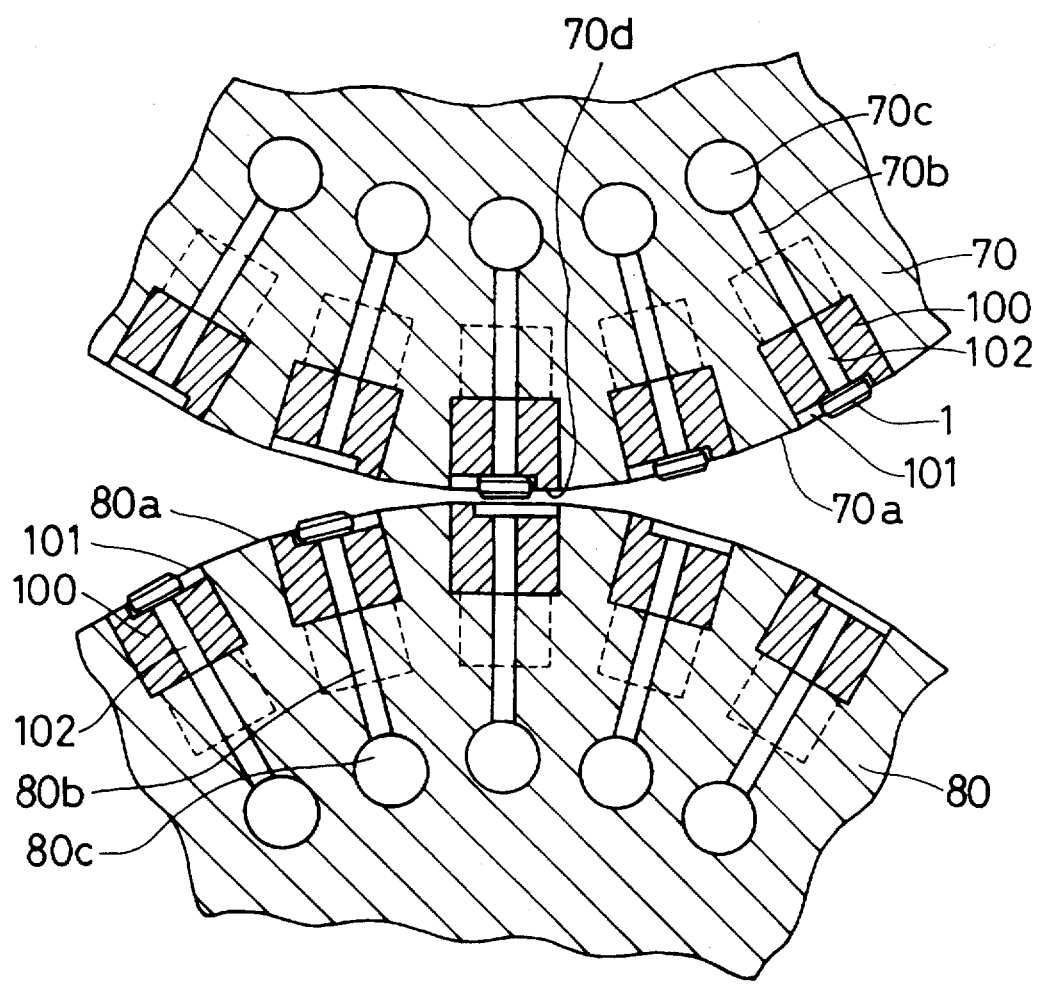
FIG. 6 is a cross-sectional side view showing a configuration of another embodiment of a conveyor for pressed articles of this invention.
Figure 7:
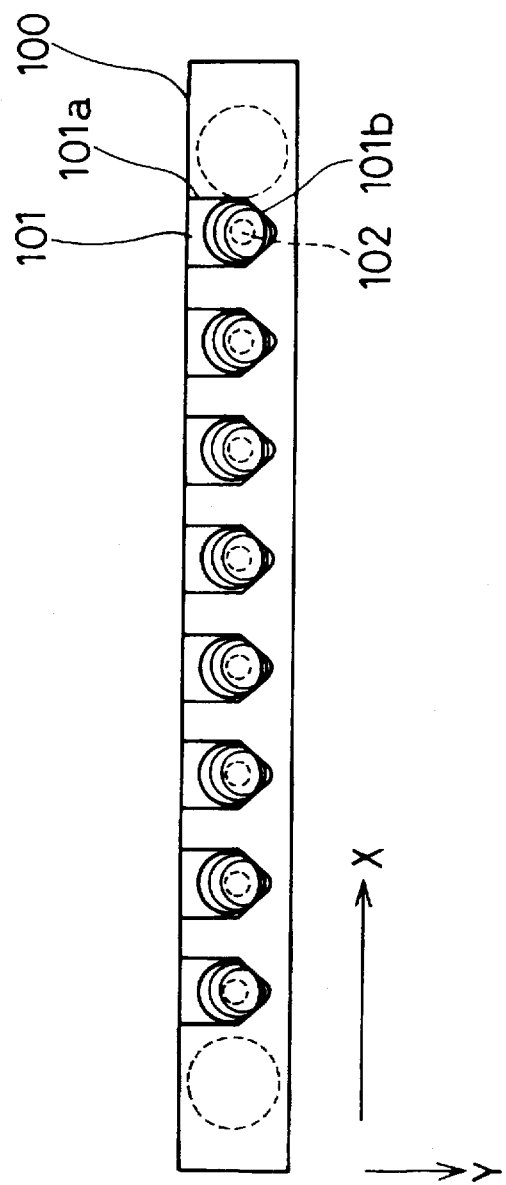
FIG. 7 is a plan view showing a shape of a block of wide use pockets 100 in FIG. 6.

Furthermore, another embodiment of the conveyor for pressed articles of this invention is described referring to FIGS. 6 and 7. FIG. 6 is a cross-sectional side view showing the conveyor for pressed articles, and FIG. 7 is a plan view showing a block 100 in FIG. 6.

As shown in FIG. 6, vertical cross-sections of conveying drums 70 and 80 are respectively equilateral polygons. The block 100 having wide use pockets 101 is fixed on each side 70a or 80a of the equilateral polygon of the conveying drum 70 or 80. On the block 100, the wide use pockets 101 and connection holes 102 are provided at positions for facing, for example, the pockets 22b of the conveying drum 20 in the above-mentioned side face examination apparatus for pressed articles. The conveying drums 70 and 80 are respectively rotatably borne around horizontal axes. The rotation of the conveying drums 70 and 80 is acceptable to be continuous or intermittent, if the movement of the sides 70a and 80a or the wide use pockets 101 or connection holes 102 of the blocks 100 are synchronized.

Furthermore, connection holes 70b and 80b, which are respectively connected to the connection holes 102 of the blocks 100, and connection pipes 70c and 80c, which are provided in axial direction, are provided on the conveying drums 70 and 80. The connection pipes 70c and 80c are respectively connected to a vacuum suction apparatus not shown in the figure. The pressed articles 1 are sucked and held in the wide use pockets 101 by negative pressure via the connection holes 70b and 80b, the connection pipes 70c and 80c and the connection holes 102 in a manner so that the cross-section of the pressed article 1 having the largest cross-sectional area is substantially parallel to the rotation axes of the conveying drums 70 and 80.

In the conveying drum 70 disposed above the conveying drum 80, when the pressed article 1 held in the wide use pocket 101 reaches to a lowest position 70d, the negative pressure in the connection hole 102 of the block 100 at the lowest portion 70d is released. Thus, the pressed article 1 falls from the wide use pocket 101 by gravity to be transferred to the conveying drum 80. Alternatively, it is preferable not only to release the negative pressure in the connection hole 102 at the lowest position 70d but also to supply positive pressure (to supply compressed air) to the connection hole 102 at the lowest portion 70d so as to transfer the pressed article 1 to the conveying drum 80, certainly.

As shown in FIGS. 6 and 7, the block 100 has a substantially rectangular cross-section in each direction. Each wide use pocket 101 has a portion 101a having sides parallel to the rotation direction of the conveying drums 70 and 80 (shown by arrow Y) and a substantially V-letter shaped portion 101b having an apex angle of about 90 degrees. The apex of the V-letter shaped portion 101b is distant a predetermined distance from the center of the connection hole 102 in the rotation direction shown by arrow Y. A side opposite to the V-letter shaped portion 101b is opened.

When the pressed article 1 is held in the wide use pockets 101, the connection hole 102 is positioned in the vicinity of the center of the pressed article 1 regardless of the size of the pressed article 1. Thus, the pressed article 1 can stably be held in the wide use pocket 101 by negative pressure via the connection hole 102.

The wide use pockets 101 are formed on the block 100, and the block 100 is interchangeably mounted on each side 70a or 80a of the equilateral polygon of the conveying drum 70 or 80. Thus, when several kinds of the blocks 100 respectively having different sizes of wide use pockets 101 are prepared, many kinds of pressed articles respectively having largely different sizes can be conveyed by the same conveyor.

In another application of this invention, if the conveyor for pressed articles comprises at least the conveying drum 50 or 70, a plane conveyor such as a belt conveyor, slats and so on can be used instead of the other conveying drum 60 or 80.

Figure 8:
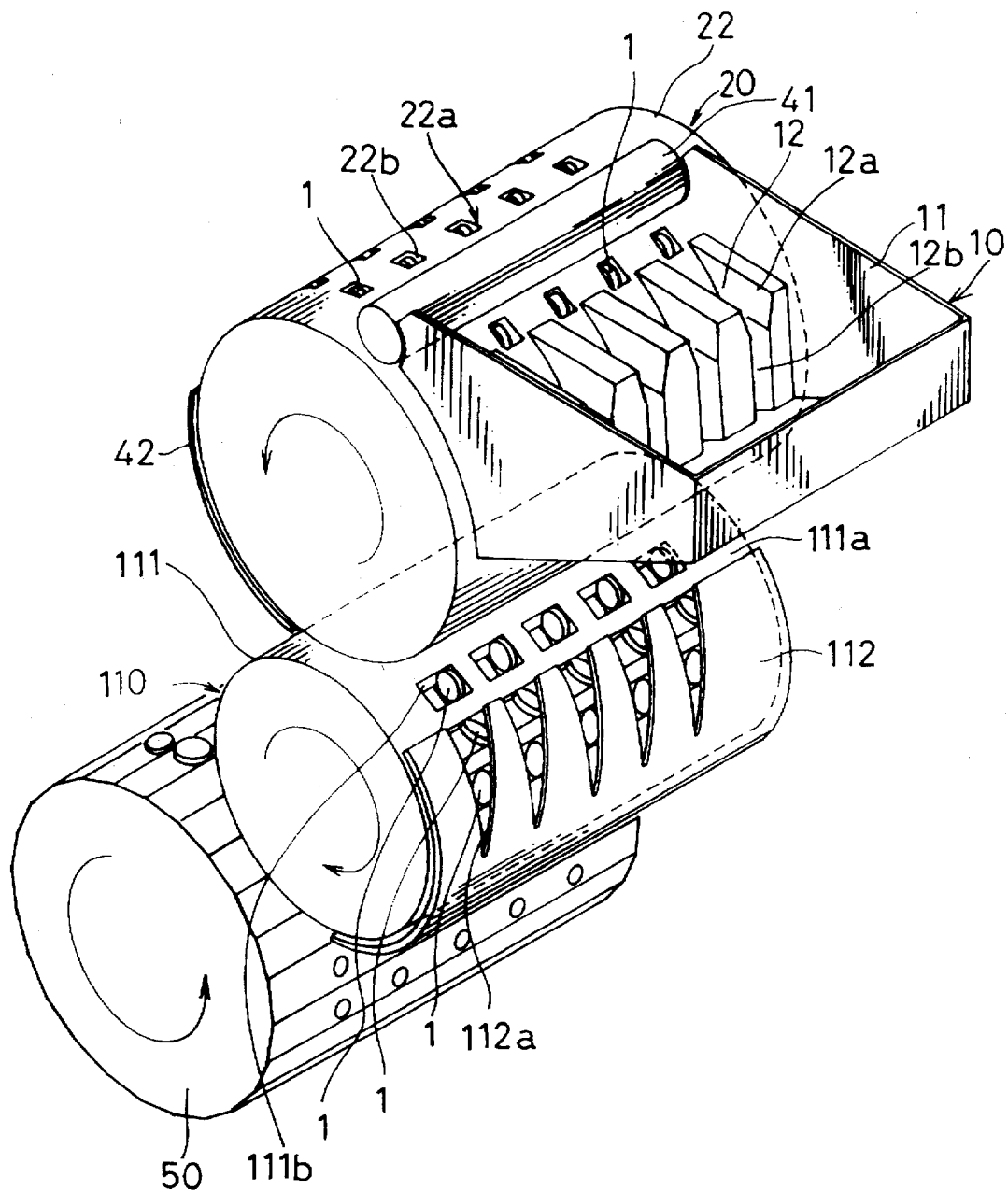
FIG. 8 is a perspective view showing a configuration of still another embodiment of a conveyor for pressed articles of this invention.

Next, still another embodiment of the conveyor for pressed articles of this invention is described referring to FIG. 8 which is a perspective view of the conveyor. As shown in FIG. 8, the conveyor comprises an arranging apparatus 10, a first conveying drum 20, a posture changing apparatus 110, and a second conveying drum 50.

The arranging apparatus 10 arranges the pressed articles 1, which are supplied at random, in a manner so that the cross-section having the largest cross-sectional area is substantially vertical. The first conveying drum 20 is disposed for facing the arranging apparatus 10 and intermittently rotated around a horizontal axis. The arranging apparatus 10 and the first conveying drum 20 are substantially the same as those of the above-mentioned side face examination apparatus for pressed articles shown in FIGS. 1 to 3, but the pressed articles rotating roller 30 and the image pickup apparatus 40 are omitted.

The posture changing apparatus 110 receives the pressed article 1 from the first conveying drum 20 in a posture such that the cross-section having the largest cross-sectional area is substantially vertical, and changes the posture of the pressed article 1 to another posture in which the cross-section having the largest area is substantially horizontal.

The second conveying drum 50 is disposed below the posture changing apparatus 110, rotated around a horizontal axis. The second conveying drum 50 receives the pressed articles from the posture changing apparatus 110 in the posture that the cross-section having the largest cross-section is substantially horizontal, and holds the pressed articles 1 as they are. The second conveying drum 50 is substantially the same as the conveying drum 50 in the conveyor for pressed articles shown in FIGS. 4 and 5.

In another application of this invention, the conveying drum 70 shown in FIGS. 6 and 7 can be used as a second conveying drum instead of the conveying drum 50.

Next, a configuration of the posture changing apparatus 110 and an operation for changing the posture of the pressed articles 1 by the posture changing apparatus 110 are described referring to FIG. 8.

The posture changing apparatus 110 comprises a rotating drum 111 rotating around a horizontal axis and a guide plate 112 disposed for facing an outer surface 111a of the drum 111 with a predetermined tolerance. The drum 111 has second pockets 111b, which are arranged for facing the first pockets of the first conveying drum 20, on its outer surface 111a. The guide plate 112 has substantially V-letter shaped grooves 112a. An edge of the guide grooves 112a is slanted from a position on upper end of the guide plate 112 where the second pockets 111b are not covered to a position where the second pockets 111b are completely covered by the guide plate 112. Each pressed article 1 protruded from the second pocket 111b contacts the slanted edge of the groove 112a.

When the pressed articles 1 are supplied at random from a hopper (not shown in the figure), they are dropped in the guide grooves 12 by the vibration applied to the arranging apparatus 10, and arranged in the guide grooves 12 in a manner so that the cross-section of the largest cross-sectional area is substantially vertical.

The pressed articles 1 arranged in the grooves 12 are transferred to the first pockets 22b, and held in the first pockets 22b in a manner so that the cross-section of the largest area is substantially vertical. The first conveying drum 20 is intermittently rotated around a horizontal axis. When the pressed articles 1 held in the first pockets 22b reaches to the lowest position of the first conveying drum 20, the pressed articles 1 are transferred to the second pockets 111b on the drum 111 of the posture changing apparatus 110.

The second pocket 111b initially holds the pressed articles 1 for protruding from the second pockets 111b in a condition that the cross-section of the pressed article 1 having the largest cross-sectional area is substantially vertical. When the drum 111 rotates around the horizontal axis, the pressed articles 1 contact the slanted edges of the grooves 112a of the guide plate 112. When the drum 111 further rotates, the pressed articles 1 gradually fall sideways in the axial direction, and finally the posture of the pressed articles 1 is changed in a manner so that the cross-section of the largest area is substantially horizontal.

The pressed articles 1 conveyed in the second pockets 111b on the drum 111 are transferred to the second conveying drum 50. The second conveying drum 50 receives the pressed articles 1 from the posture changing apparatus 110 in a posture that the cross-section of the largest area is substantially horizontal, and holds the pressed articles 1 on the sides 501 in a manner so that the cross-section of the largest area is substantially parallel to the rotation axis of the second conveying drum. With respect to the driving of the drum 111, it is sufficient that the second pockets 111b are moved in synchronism with the movement of the first pocket 22b. The drum 111 can alternatively be driven by a intermittent driving method and a continuous driving method.

Since the conveyor for pressed articles configured above comprises the arranging apparatus 10, the first conveying drum 20 and the posture changing apparatus 110, it can arrange and convey the pressed articles 1, which are supplied at random, in a manner so that the cross-section having the largest area is substantially parallel to the rotation axis of the conveying drum. Accordingly, the conveyor for pressed articles of this invention can be applied not only for the external appearance examination apparatus, but also a printing apparatus, PTP packaging apparatus, and so on.

Figure 9:
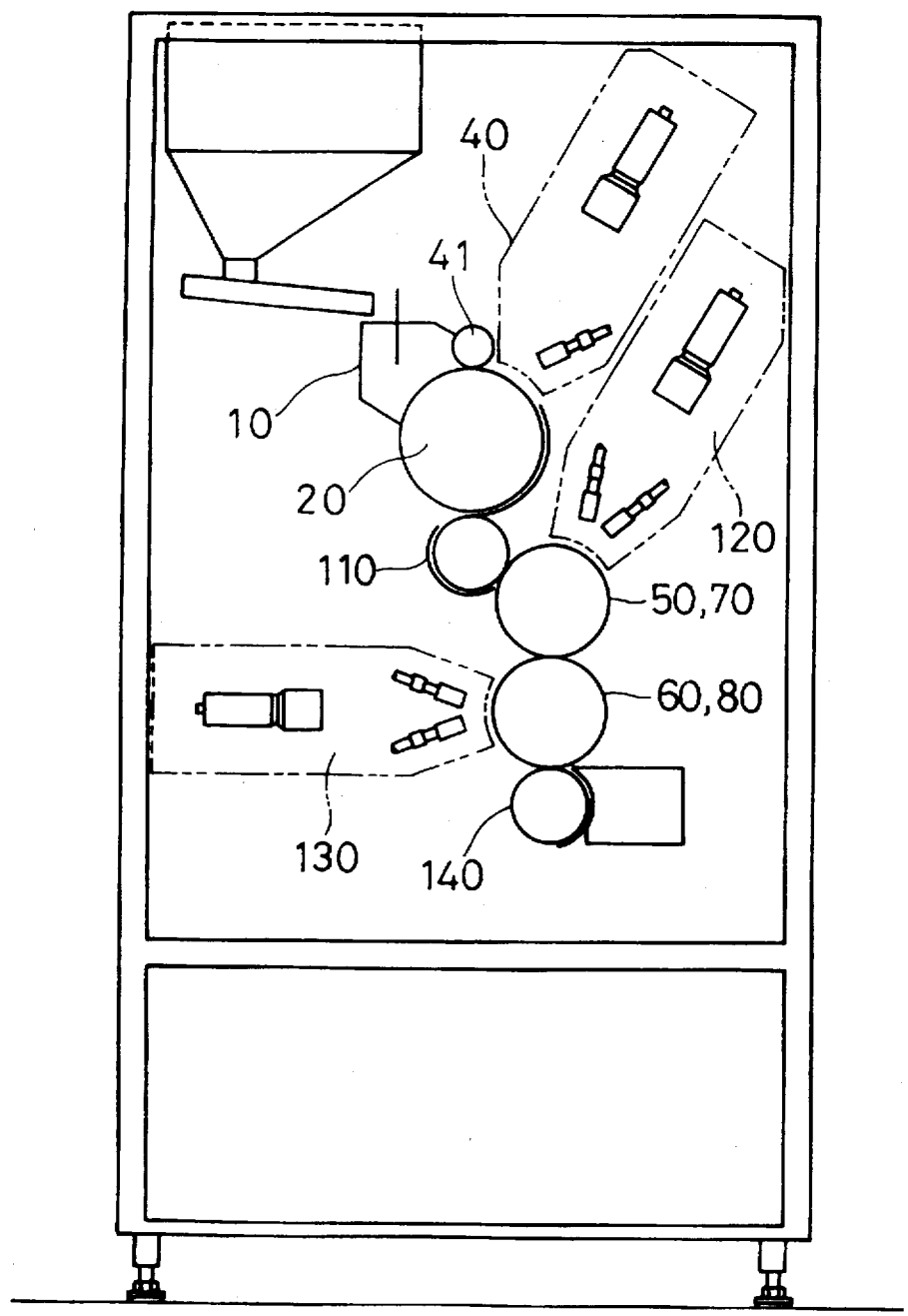
FIG. 9 is a side view showing positions of respective units in an embodiment of an external appearance examination apparatus for pressed articles of this invention.
Figure 10:
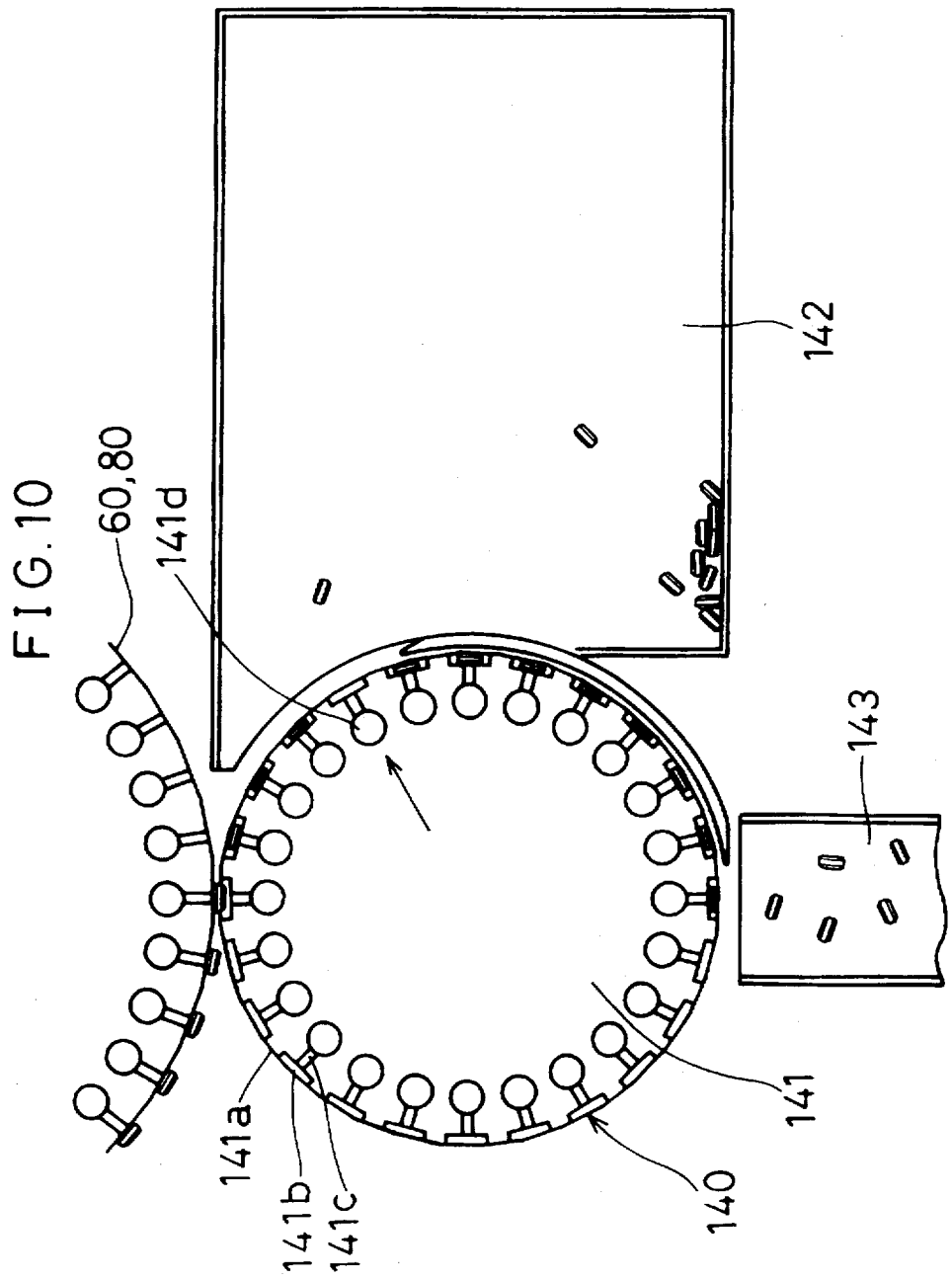
FIG. 10 is a cross-sectional side view showing a configuration of an inferior article removing apparatus in FIG. 9.

Next, an embodiment of an external appearance examination apparatus for pressed articles using the above-mentioned side face examination apparatus and conveyor for pressed articles is explained referring to FIGS. 9 and 10. FIG. 9 is a side view showing positions of respective units in the external appearance examination apparatus, and FIG. 10 is a cross-sectional side view showing a configuration of an inferior article removing apparatus. In the following explanation, elements designated by the same numerals as those of the above-mentioned embodiments of the side face examination apparatus for pressed articles and the conveyor for pressed articles are substantially the same, so that the explanation of them are omitted.

As shown in FIG. 9, the external appearance examination apparatus for pressed articles comprises an arranging apparatus 10 for arranging pressed articles 1 (not shown in FIG. 9) in a manner so that a cross-section having the largest area is substantially vertical. A first conveying drum 20 is disposed for facing the arranging apparatus 10 and is intermittently rotated around a horizontal axis. A pressed article rotating roller 30 (not shown in FIG. 9) is provided inside the first conveying drum 20 and rotates the pressed articles 1 at least more than one turn around a horizontal axis. A first image pickup apparatus 40 is disposed for facing an outer surface of the first conveying drum 20 and picks up a picture of side faces of the pressed articles 1. A posture changing apparatus 110 is disposed below the first conveying drum 20 and changes postures of the pressed articles 1 received from the first conveying drum 20 under a posture that the cross-section having the largest area is substantially vertical to another posture that the cross-section is substantially horizontal. A second conveying drum 50 or 70 is disposed below the posture changing apparatus 110, is rotated around a horizontal axis, and holds the pressed articles 1 in a posture that the cross-section of the largest area is substantially parallel to its axis. A second image pickup apparatus 120 is disposed for facing an outer surface of the second conveying drum 50 or 70 and for picking up a picture of first surfaces of the pressed articles 1 which are parallel to the cross-section of the largest area. A third conveying drum 60 or 80 is disposed below the second conveying drum 50 or 70, is rotated around a horizontal axis, and holds the pressed articles 1 in a posture that the cross-section of the largest area is substantially parallel to its axis. And, a third image pickup apparatus 130 is disposed to face an outer surface of the third conveying drum 60 or 80 and picks up a picture of second surfaces of the pressed articles which corresponds to the back face of the first surfaces and are parallel to the cross-section of the largest area.

Furthermore, an inferior article removing apparatus 140 for removing an inferior article which is found to be inferior on at least one of the side face and first and second surfaces is provided below the third conveying drum 60 or 80, as occasion demands. As mentioned above, the first conveying drum 20 is intermittently driven. However, the posture changing apparatus 110, the second conveying drum 50 or 70, the third conveying drum 60 or 80 and the inferior article removing apparatus 140 can be driven either by the intermittent driving method and the continuous driving method, as long as the movement of, for example, the first and second pockets are synchronized.

Next, a configuration and operation of the inferior article removing apparatus 140 is described referring to FIG. 10. As shown in FIG. 10, the inferior article removing apparatus 140 is to be disposed below the third conveying drum 60 or 80. The inferior article removing apparatus 140 comprises a drum 141 rotating around a horizontal axis, an inferior article removing shoot 142 disposed at a side of the drum 141, and an excellent article conveying shoot 143 disposed for facing the bottom portion of the drum 141. The drum 141 has third pockets 141b having an area larger than the largest cross-sectional area of the pressed articles 1 and provided at positions facing the second connection holes or second wide use pockets of the third conveying drum 60 or 80 and third connection holes 141c provided in the third pockets.

When an inferiority is found on at least one of the side face, first and second surfaces of a pressed article 1, compressed air is blasted against the pressed article 1 via the connection hole at a position 141d facing the inferior article removing shoot 142. The pressed article 1 is blown into the inferior article removing shoot 142 and removed from the external appearance examination process. On the other hand, pressed articles 1, which are not found to be inferior on the side face, first and second surfaces, are conveyed to the lowest portion of the drum 141, dropped into the excellent article conveying shoot 143, and conveyed to a next process.

The external appearance examination apparatus configured above includes the afore-mentioned side face examination apparatus and the conveyor for pressed articles of this invention. Furthermore, the posture changing apparatus 110 is provided below the first conveying drum 20. The posture changing apparatus 110 changes the posture of the pressed articles 1 in a manner so that the direction of the cross-section having the largest area is changed from substantially vertical to substantially horizontal. The second conveying drum 50 or 70 is provided below the posture changing apparatus 110, and the third conveying drum 60 or 80 is provided below the second conveying drum 50 or 70. The front and rear surfaces of the pressed articles 1 conveyed by the second conveying drum 50 or 70 and the third conveying drum 60 or 80 are examined by the second and third image pickup apparatuses 120 and 130. As a result, not only the side face but also the front and rear faces of the pressed articles 1 can be examined by the external appearance examination apparatus of this invention. Furthermore, the inferior article removing apparatus is provided below the third conveying drum 60 or 80, so that an inferior article, which is found to be inferior on at least one of the side face, first and second surfaces, can be removed.

Figure 11:
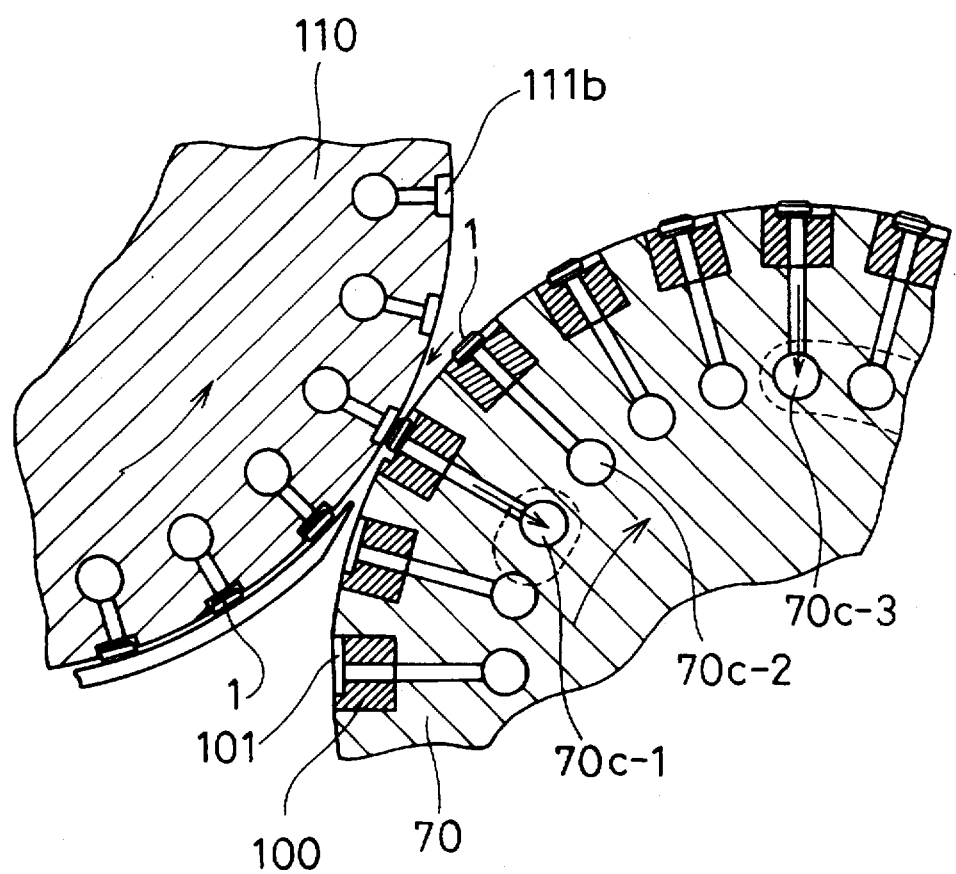
FIG. 11 is a cross-sectional side view showing a positioning method of a pressed article 1 in a conveying drum 70 using wide use pockets 101.
Figure 12A:
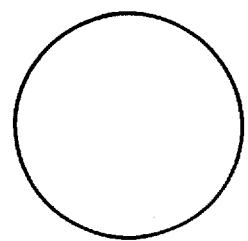
FIG. 12(a) is a plan view of an embodiment of a general pressed article such as a tablet having a substantially circular cross-section when the substantially circular cross-section is to be horizontal.
Figure 12B:
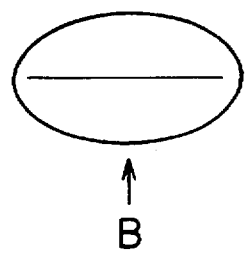
FIG. 12(b) is a side view of the pressed article of FIG. 12(a)
Figure 13A:
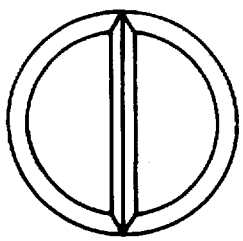
FIG. 13 (a) is a plan view of another embodiment of a general pressed article such as a tablet having a substantially circular cross-section when the substantially circular cross-section is to be horizontal.
FIG. 13(b) is a side view of the pressed article of FIG. 13(a)
Figure 13B:
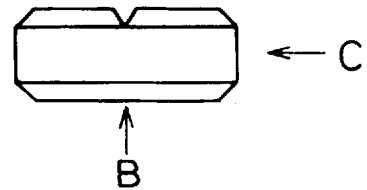
Figure 14:
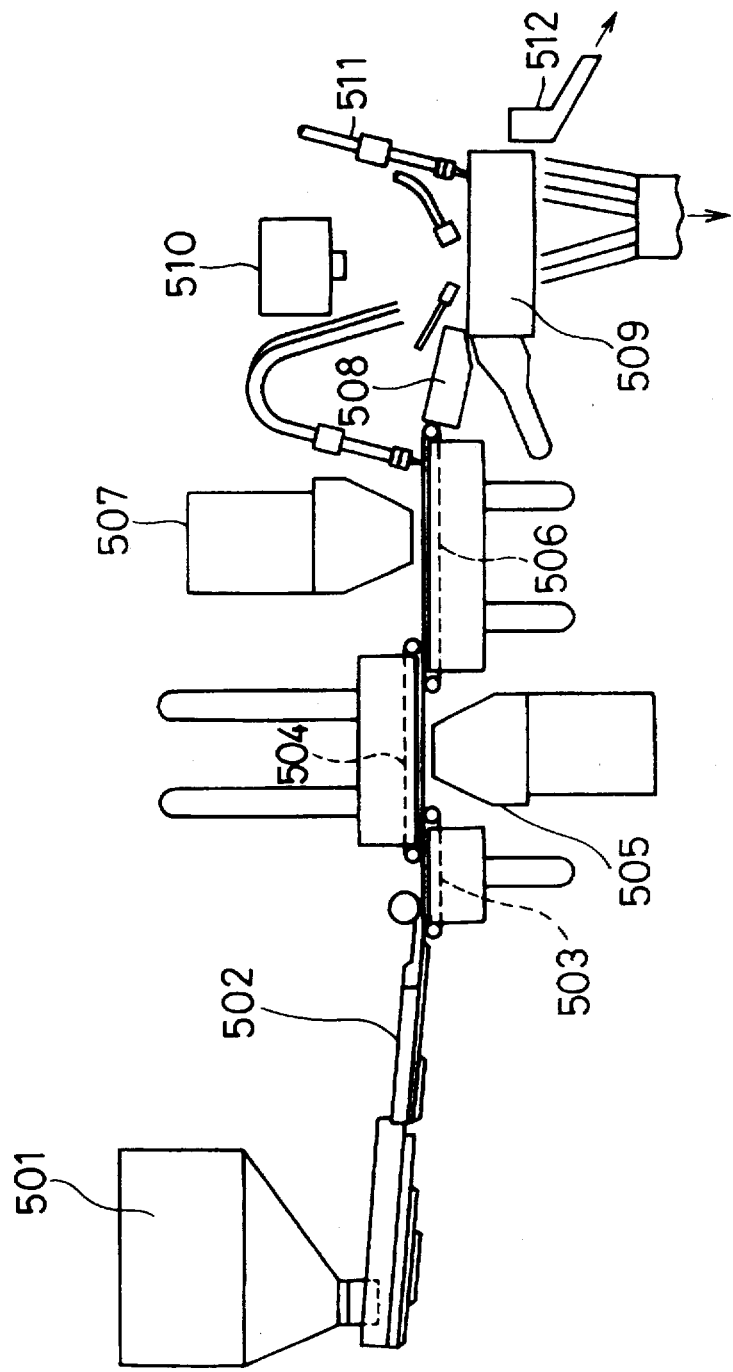
FIG. 14 is a side view showing a configuration of a conventional external appearance examination apparatus for pressed articles.

When the conveying drum 70 having the blocks 100 is used as the second conveying drum, the pressed articles 1 can be positioned in the wide use pockets 101 by using a method shown in FIG. 11. For example, when the pressed article 1 is received from the posture changing apparatus 110, the pressed article 1 is forcibly sucked in the wide use pocket 101 of the conveying drum 70 by the negative pressure in the connection hole 70c-1. At this time, the position of the pressed article 1 in the wide use pocket 101 is not necessarily constant. Therefore, the negative pressure is once released when the wide use pocket 101 reaches at a position of the adjoining connection hole 70c-2. The pressed article 1 is slid in the wide use pocket 101 by own weight or by blowing compressed air. The side face of the pressed article 1 contacts the edges of the apex side of the V-letter shaped portion 101b of the wide use pocket 101. When the wide use pocket 101 containing the pressed article 1 under such a condition reaches a position of the connection hole 70c-3, the sucking by the negative pressure is reopened. As a result, in a position forward of the connection hole 70c-3, the pressed article 1 is stably held in a condition that the side face always contacts the edges of the apex side of the V-letter shaped portion 101b of the wide use pocket 101. As a result, the pressed articles 1 are forcibly positioned. This method can be used when the pressed articles 1 are transferred between the second conveying drum 70 and the third conveying drum 80. As a result, in the external appearance examination of the front and rear surfaces of the pressed articles 1, the positions of the pressed articles 1 against the wide use pockets 101 become stable, quality judgement becomes easy and the accuracy of the quality judgement increases.

What is claimed is:

1. A side face examination apparatus for pressed articles comprising:

an arranging apparatus for arranging pressed articles, which are supplied at random, in a manner so that a cross-section of one of said pressed articles having a largest area is substantially vertical, and having a plurality of guide grooves which have a width wider by a predetermined tolerance than a width of said pressed articles in a direction perpendicular to said cross-section;

a conveying drum intermittently rotated around a horizontal axis, and having pockets arranged for facing said guide grooves and holding said pressed articles, which are arranged by said arranging apparatus, in a manner so that said cross-section is substantially vertical;

a pressed article rotating roller disposed at a predetermined position in the inside of said conveying drum, and rotating said pressed articles in said pockets stopped at said predetermined position more than one turn around their horizontal axes; and an image pickup apparatus disposed for facing an outer surface of said conveying drum at said predetermined position, and picking up picture images of side faces of said pressed articles in said pockets.

2. The side face examination apparatus for pressed articles in accordance with claim 1, wherein said conveying drum comprises a fixed hollow inner sleeve and an outer sleeve rotatably engaged with an outer surface of said inner sleeve with a predetermined tolerance; said pockets are provided on said outer sleeve; connection holes or slits are provided at portions of said inner sleeve facing said guide grooves; and an inside of said inner sleeve is connected to a vacuum suction apparatus.

3. The side face examination apparatus for pressed articles in accordance with claim 2, wherein said pressed article rotating roller is rotatably borne on said inner sleeve, and has a plurality of larger diameter portions corresponding to the arrangement of said pockets, said larger diameter portions are protruded from the outer periphery of said inner sleeve.

4. The side face examination apparatus for pressed articles in accordance with claim 3, wherein a width of said larger diameter portions of said pressed article rotating roller in a direction parallel to a rotation axis thereof is wider than a width of said pockets in said direction, and centers of said larger diameter portions are inconsistent with centers of said pockets.

5. The side face examination apparatus for pressed articles in accordance with claim 1, wherein openings of said pockets are formed substantially as parallelograms, a pair of parallel sides are parallel to said horizontal axis of said conveying drum and the other parallel sides are inclined against said horizontal axis of said conveying drum.

6. The side face examination apparatus for pressed articles in accordance with claim 1, wherein each of said guide grooves of said arranging apparatus includes a slanted portion and a straight portion, a width in said slanted portion becomes gradually narrower when the position progresses downward, a width in said straight portion is a width wider by a predetermined tolerance than a width of said pressed articles in a direction perpendicular to said cross-section having the largest area, and a vibration is applied to said arranging apparatus.

7. The side face examination apparatus for pressed articles in accordance with claim 1, wherein the conveyor for pressed articles comprises:

a conveying drum having an equilateral polygonal cross-section in a vertical direction, and rotated around a horizontal axis; and connection holes provided at predetermined positions on each side of said equilateral polygon for holding pressed articles by negative pressure via said connection holes in a manner so that a cross-section of said pressed article having a largest area is substantially parallel to said horizontal axis.

8. The side face examination apparatus for pressed articles in accordance with claim 1, wherein the conveyor for pressed articles comprises:

a conveying drum having an equilateral polygonal cross-section in a vertical direction, and rotated around a horizontal axis; and connection holes and wide use pockets provided at predetermined positions on each side of said equilateral polygon for holding pressed articles by negative pressure via said connection holes in said pockets in a manner so that a cross-section of said pressed article having a largest area is substantially parallel to said horizontal axis.

9. A conveyor for pressed articles comprising:

a conveying drum having an equilateral polygonal cross-section in a vertical direction, and rotated around a horizontal axis; and connection holes and wide use pockets provided at predetermined positions on each side of said equilateral polygon for holding pressed articles by negative pressure via said connection holes in said pockets in a manner so that a cross-section of said pressed article having a largest area is substantially parallel to said horizontal axis;

wherein each of said wide use pockets has a portion parallel to a rotation direction of said conveying drum and a substantially V-letter shaped portion having an apex angle of substantially 90 degrees which has an apex at a point which is a predetermined distance from center of said connection hole in said rotation direction.

10. A conveyor for pressed articles comprising:

a conveying drum having an equilateral polygonal cross-section in a vertical direction, and rotated around a horizontal axis; and connection holes and wide use pockets provided at predetermined positions on each side of said equilateral polygon for holding pressed articles by negative pressure via said connection holes in said pockets in a manner so that a cross-section of said pressed article having a largest area is substantially parallel to said horizontal axis;

wherein each of said wide use pockets has a portion parallel to a rotation direction of said conveying drum and a substantially V-letter shaped portion having an apex angle of substantially 90 degrees which has an apex at a point which is a predetermined distance from center of said connection hole in said rotation direction, and further wherein said wide use pockets are formed on a block having a substantially rectangular cross-section in each direction, and each block is interchangeably fixed on each side of said equilateral polygon of said conveying drum.

11. A conveyor for pressed articles comprising:

an arranging apparatus for arranging pressed articles, which are supplied at random, in a manner so that a cross-section of said pressed articles having a largest area is substantially vertical, and having a plurality of guide grooves which have a width wider by a predetermined tolerance than a width of said pressed articles in a direction perpendicular to said cross-section;

a first conveying drum intermittently rotated around a horizontal axis, and having first pockets arranged for facing said guide grooves and holding said pressed articles, which are arranged by said arranging apparatus, in a manner so that said cross-section is substantially vertical;

a posture changing apparatus disposed below said first conveying drum, having second pockets arranged for facing said first pockets, and changing posture of said pressed articles in a manner so that a direction of said cross-section of said pressed article having the largest area is changed from substantially vertical to substantially horizontal; and a second conveying apparatus disposed below said posture changing apparatus, having an equilateral polygonal cross-section in the vertical direction, and rotated around a horizontal axis, wherein connection holes are provided at predetermined positions facing said second pockets on each side of said equilateral polygon for holding said pressed articles in a manner so that said cross-section of said pressed articles is substantially parallel to said horizontal axis by negative pressure via said connection holes.

12. The conveyor for pressed articles in accordance with claim 10 or 11, wherein each of said guide grooves of said arranging apparatus includes a slanted portion and a straight portion, wherein a width in said slanted portion becomes gradually narrower when a position progresses downward, a width in said straight portion is a width wider by a predetermined tolerance than a width of said pressed articles in a direction perpendicular to said cross-section having the largest area, and a vibration is applied to said arranging apparatus.

13. The conveyor for pressed articles in accordance with claim 11, wherein said first conveying drum comprises a fixed hollow inner sleeve and an outer sleeve rotatably engaged with an outer surface of said inner sleeve with a predetermined tolerance; said first pockets are provided on said outer sleeve; connection holes or slits are provided at portions of said inner sleeve facing said guide grooves; and an inside of said inner sleeve is connected to a vacuum suction apparatus.

14. The conveyor for pressed articles in accordance with claim 11, wherein said posture changing apparatus comprises a rotating drum rotating around a horizontal axis and having said second pockets, and a guide plate provided for facing an outer surface of said drum with a predetermined tolerance, said guide plate has slanted grooves which contacts pressed articles protruded from said second pockets and slanted from a position on upper end of said guide plate where said second pockets are not covered to a position where said second pockets are completely covered.

15. A conveyor for pressed articles comprising:

an arranging apparatus for arranging pressed articles, which are supplied at random, in a manner so that a cross-section of said pressed articles having a largest area is substantially vertical, and having a plurality of guide grooves which have a width wider a predetermined tolerance than a width of said pressed articles in a direction perpendicular to said cross-section;

a first conveying drum intermittently rotated around a horizontal axis, and having first pockets arranged for facing said guide grooves and holding said pressed articles, which are arranged by said arranging apparatus, in a manner so that said cross-section is substantially vertical;

a posture changing apparatus disposed below said first conveying drum, having second pockets arranged for facing said first pockets, and changing posture of said pressed articles in a manner so that a direction of said cross-section of said pressed article having the largest area is changed from substantially vertical to substantially horizontal: and a second conveying apparatus disposed below said posture changing apparatus, having an equilateral polygonal cross-section in the vertical direction, and rotated around a horizontal axis, wherein connection holes and wide use pockets are provided at predetermined positions facing said second pockets on each side of said equilateral polygon for holding said pressed articles in a manner so that said cross-section of said pressed articles is substantially parallel to said horizontal axis by negative pressure via said connection holes.

16. The conveyor for pressed articles in accordance with claim 15, wherein each of said wide use pocket has a portion parallel to a rotation direction of said second conveying drum and a substantially V-letter shaped portion having an apex angle of substantially 90 degrees which has an apex at a point distant a predetermined distance from center of said connection hole in said rotation direction.

17. The conveyor for pressed articles in accordance with claim 15, wherein said wide use pockets are formed on a block having a substantially rectangular cross-section in each direction, and each block is interchangeably fixed on each side of said equilateral polygon of said second conveying drum.

18. An external appearance examination apparatus for pressed articles comprising:

an arranging apparatus for arranging pressed articles, which are supplied at random, in a manner so that a cross-section of said pressed articles having a largest area is substantially vertical, and having a plurality of guide grooves which have a width wider a predetermined tolerance than a width of the pressed articles in a direction perpendicular to said cross-section;

a first conveying drum intermittently rotated around a horizontal axis, and having first pockets arranged for facing said guide grooves and holding said pressed articles, which are arranged by said arranging apparatus, in a manner so that said cross-section is substantially vertical;

a pressed article rotating roller disposed at a predetermined first position in the inside of said first conveying drum, and rotating said pressed articles in said pockets stopped at said predetermined first position more than one turn around horizontal axes;

a first image pickup apparatus disposed for facing an outer surface of said first conveying drum at said first predetermined position, and picking up pictures of side faces of said pressed articles in said first pockets;

a posture changing apparatus disposed below said first conveying drum, having second pockets arranged for facing said first pockets, and changing postures of pressed articles in a manner so that a direction of said cross-section of said pressed articles is changed from substantially vertical to substantially horizontal;

a second conveying drum disposed below said posture changing apparatus, having an equilateral polygonal cross-section in the vertical direction, and rotated around a horizontal axis, wherein first connection holes are provided at predetermined positions facing said second pockets on each side of said equilateral polygon, and hold said pressed articles by negative pressure via said first connection holes in a manner so that said cross-sections of said pressed articles are substantially parallel to said horizontal axis;

a second image pickup apparatus disposed for facing an outer surface of said second conveying drum at a second predetermined position, and picking up pictures of first faces of said pressed articles;

a third conveying drum disposed below said second conveying drum, having an equilateral polygonal cross-section in the vertical direction and rotated around a horizontal axis, wherein second connection holes are provided at predetermined positions facing said first connection holes on each side of said equilateral polygon, and hold said pressed articles, which are received from said second conveying drum, by negative pressure via said second connection holes in a manner so that said cross-sections of said pressed articles are substantially parallel to said axis; and a third image pickup apparatus disposed for facing an outer surface of said third conveying drum at a third predetermined position, and picking up pictures of second faces of said pressed articles, which are back sides of said first faces.

19. An external appearance examination apparatus for pressed articles comprising:

an arranging apparatus for arranging pressed articles, which are supplied at random, in a manner so that a cross-section of said pressed articles having a largest area is substantially vertical, and having a plurality of guide grooves which have a width wider by a predetermined tolerance than a width of the pressed articles in a direction perpendicular to said cross-section;

a first conveying drum intermittently rotated around a horizontal axis, and having first pockets arranged for facing said guide grooves and holding said pressed articles, which are arranged by said arranging apparatus, in a manner so that said cross-section is substantially vertical;

a pressed article rotating roller disposed at a predetermined first position in an inside of said first conveying drum, and rotating said pressed articles in said pockets stopped at said predetermined first position more than one turn around horizontal axes of said pressed articles;

a first image pickup apparatus disposed for facing an outer surface of said first conveying drum at said first predetermined position, and picking up pictures of side faces of said pressed articles in said first pockets;

a posture changing apparatus disposed below said first conveying drum, having second pockets arranged for facing said first pockets, and changing postures of pressed articles in a manner so that a direction of said cross-section of said pressed articles is changed from substantially vertical to substantially horizontal;

a second conveying drum disposed below said posture changing apparatus, having an equilateral polygonal cross-section in the vertical direction, and rotated around a horizontal axis, wherein first connection holes and first wide use pockets are provided at predetermined positions facing said second pockets on each side of said equilateral polygon and hold said pressed articles by negative pressure via said first connection holes in a manner so that said cross-section of said pressed article is substantially parallel to said horizontal axis;

a second image pickup apparatus disposed for facing an outer surface of said second conveying drum at a second predetermined position, and picking up pictures of first faces of said pressed articles;

a third conveying drum disposed below said second conveying drum, having an equilateral polygonal cross-section in the vertical direction and rotated around a horizontal axis, wherein second connection holes and second wide use pockets are provided at predetermined positions facing said first connection holes on each side of said equilateral polygon, and hold said pressed articles, which are received from said second conveying drum, by negative pressure via said second connection holes in a manner so that said cross-section of said pressed article is substantially parallel to said axis; and a third image pickup apparatus disposed for facing an outer surface of said third conveying drum at a third predetermined position, and picking up pictures of second faces of said pressed articles, which are back sides of said first faces.

20. The external appearance examination apparatus for pressed articles in accordance with claim 18 or 19, wherein said first conveying drum comprises a fixed hollow inner sleeve and an outer sleeve rotatably engaged with an outer surface of said inner sleeve with a predetermined tolerance; said pockets are provided on said outer sleeve; connection holes or slits are provided at portions of said inner sleeve facing said guide grooves; and the inside of said inner sleeve is connected to a vacuum suction apparatus.

21. The external appearance examination apparatus for pressed articles in accordance with claim 20, wherein said pressed article rotating roller is rotatably borne on said inner sleeve, has a plurality of larger diameter portions corresponding to the arrangement of said pockets, said larger diameter portions are protruded from the outer periphery of said inner sleeve.

22. The external appearance examination apparatus for pressed articles in accordance with claim 21, wherein a width of said larger diameter portions of said pressed article rotating roller in a direction of the rotation axis is wider than a width of said pockets in the same direction, and centers of said larger diameter portions are inconsistent with centers of said pockets.

23. The external appearance examination apparatus for pressed articles in accordance with claim 18 or 19, wherein openings of said pockets are formed substantially as parallelograms, a pair of parallel sides are parallel to the rotation axis of said first conveying drum and other parallel sides are inclined against the rotation axis of said first conveying drum.

24. The external appearance examination apparatus for pressed articles in accordance with claim 18 or 19, wherein each of said guide grooves of said arranging apparatus includes a slanted portion and a straight portion, wherein a width in said slanted portion becomes gradually narrower when a position progresses downward, a width in said straight portion is a width wider by a predetermined tolerance than a width of said pressed articles in a direction perpendicular to said cross-section having the largest area, and a vibration is applied to said arranging apparatus.

25. The external appearance examination apparatus for pressed articles in accordance with claim 18 or 19, wherein said posture changing apparatus comprises a rotating drum rotating around a horizontal axis and having said second pockets, and a guide plate provided for facing an outer surface of said drum with a predetermined tolerance, said guide plate has slanted grooves which contacts pressed articles protruded from said second pockets and slanted from a position on an upper end of said guide plate where said second pockets are not covered to a position where said second pockets are completely covered.

26. The external appearance examination apparatus for pressed articles in accordance with one of claims 18 or 19, further comprising an inferior article removing apparatus which is disposed below said third conveying drum, has third pockets provided at positions facing said second connection holes or said second wide use pockets and having an area larger than a largest cross-sectional area of said pressed articles and has third connection holes provided in said third pockets, and removes a pressed article in which an inferiority is found on at least one of said side face, first surface and second surface by blasting compressed air through said third connection holes.

27. The external appearance examination apparatus for pressed articles in accordance with claim 19, wherein each of said first and second wide use pocket has a portion parallel to the rotation direction of said and third second conveying drums and a substantially V-letter shaped portion having an apex angle of substantially 90 degrees which has an apex at a point distant a predetermined distance from a center of said first and second connection hole in said rotation direction.

28. The external appearance examination apparatus for pressed articles in accordance with claim 27, wherein said first and second wide use pockets are formed on blocks having a substantially rectangular cross-section in each direction, and each block is interchangeably fixed on a side of said equilateral polygon of said second and third conveying drums.

* * * * *